United States Patent [19]

Savage et al.

[11] Patent Number: 4,551,479
[45] Date of Patent: Nov. 5, 1985

[54] COMPOUNDS WITH ANTI-CONVULSIVE PROPERTIES

[75] Inventors: David S. Savage, Glasgow; James Redpath, Bishopbriggs, both of Scotland

[73] Assignee: Akzo N.V., Arnhem, Netherlands

[21] Appl. No.: 592,102

[22] Filed: Mar. 22, 1984

[30] Foreign Application Priority Data

Mar. 29, 1983 [NL] Netherlands ................... 8301096

[51] Int. Cl.[4] .......................................... A61K 31/135
[52] U.S. Cl. .................................................. 514/657
[58] Field of Search ................. 564/427; 424/330; 514/657

[56] References Cited
U.S. PATENT DOCUMENTS 4,008,277 2/1977 Hewitt et al. .................... 424/330

Primary Examiner—Stanley J. Friedman
Attorney, Agent, or Firm—Abelman, Frayne, Rezac & Schwab

[57] ABSTRACT

The present invention relates to the use of a compound of the general formula I

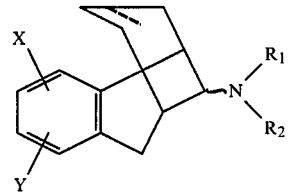

wherein $R_1$ and $R_2$ represent hydrogen or a lower alkyl group (1-4 C), preferably methyl, ethyl, propyl or isopropyl, the broken line indicates an optional extra bond, and X and Y represent hydrogen, alkyl (1-4 C) or halogen (preferably fluorine), or a pharmaceutically acceptable acid addition salt thereof, for its anti-convulsive property.

2 Claims, No Drawings

COMPOUNDS WITH ANTI-CONVULSIVE PROPERTIES

The present invention relates to a novel use for compounds having the general formula I:

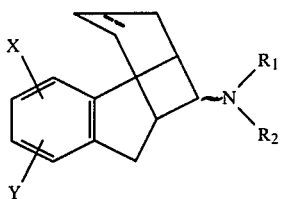

wherein $R_1$ and $R_2$ represent hydrogen or a lower alkyl group (1–4 C), preferably methyl, ethyl, propyl or isopropyl, the broken line indicates an optional extra bond, and X and Y represent hydrogen, alkyl (1–4 C) or halogen (preferably fluorine, or a pharmaceutically acceptable acid addition salt thereof.

Some of these compounds are known from U.S. Pat. No. 4,008,277, and possess anorectic and antidepressive properties; others are known from Chem.Pharm.Bull. 18, 75 (1970).

Compounds I wherein the broken line does not represent an extra bond and at least one of the substituents X or Y represents a substituent other than hydrogen are new compounds.

Surprisingly, it has now been found that the present compounds of formula I possess outstanding anti-convulsive properties. In particular they are suitable for the treatment of epilepsy, a form of cramp which—in its most serious form—is accompanied by loss of consciousness.

The anti-convulsive properties of the compounds according to formula I and acid addition salts thereof are revealed in a number of tests—customary for testing anti-convulsive properties—on test animals. An important aspect of the present anti-convulsive compounds is the fact that they all possess low sedative properties. Sedative properties produce an extremely undesired side-effect in the case of what are currently the most active anti-convulsive compounds, namely compounds belonging to the group of the benzodiazepines. It has furthermore been found that the anti-convulsive action of the present compounds does not arise from the action of the compound on the benzodiazepine receptors present in the body. The anti-convulsive effect of, for example, diazepam can be completely counteracted by administration of a known benzodiazepine antagonist (Ro 15-1788); this antagonist however has no effect whatsoever in respect of the action of the present compounds.

The table which follows gives an impression of the effectiveness of the present compounds in comparison with three known anti-convulsive substances:

TABLE

| Compound | Anti-convulsive properties | | Neurotoxicity and sedation | |
|---|---|---|---|---|
| | Electroshock test $ED_{200}$ i.p.[1] | PTZ test $ED_{50}$ i.p. mg/kg[2] | Rotarod $ED_{50}$ i.p. mg/kg | Shuttle box $ED_{50}$ i.p. mg/kg |
| Reference substances: | | | | |
| diazepam | 14 | 0.5 | 1.3 | 8 |
| sodium salt of valproic acid | 180 | 30 | 230 | 350 |
| diphenyl hydantoin | 15 | 22 | 100 | 100 |
| Substances according to the invention: | | | | |
| 1. | 11 | 10 | 70 | >46 |
| 2. | 7 | 10 | 20 | 40 |

[1] The $ED_{200}$ is the dose of the test compound (in mg/kg) which necessitates a 100% increase of the current intensity to bring about a tonic convulsion in 50% of the test animals.
[2] Pentylenetetrazole (i.e. PTZ) directly activates the nerve endings, leading to a cramp condition.

It can be seen from the table that the compounds according to the present invention have a powerful anti-convulsive action and also possess a markedly lower neurotoxicity than, for example, diazepam.

The compounds according to the general formula I and acid addition salts thereof can be prepared by the method described in U.S. Pat. No. 4,008,277 and Chem.-Pharm.Bull. 18, 75 (1970).

The anti-convulsive compounds I including diastereoisomeric forms, enantiomers and mixtures thereof can be administered both enterally and parenterally.

Mixed with suitable auxiliaries they can be processed into solid dosage forms, such as tablets, pills, dragees or capsules, or into solutions, emulsions or suspensions for oral or parenteral administration.

The compounds I which are used preferably are: dl-11-anti-dimethylamino-benzo(b)bicyclo[3.3.1]nona-3,6a(10a)diene, acid addition salts thereof as well as the separate optical enantiomers thereof, and the corresponding 11-syn compounds.

The most effective anti-convulsive daily dose of the present compounds is between 0.1 and 15 mg/kg body weight, the oral dose preferably being between 0.2 and 15 mg/kg body weight and the parenteral dose preferably between 0.1 and 5 mg/kg body weight.

For human administration, a daily dose of 5–1000 mg is preferred, whereby 10–1000 mg and preferably 50–500 mg is recommended for oral administration and 5–50 mg for parenteral administration.

EXAMPLE

Tablet form

A 130 mg tablet having the following composition:

potato flour: 13.0 mg lactose: 63.7 mg hydroxypropylcellulose: 2.6 mg magnesium stearate: 0.7 mg compound 1 from the preceding table: 50.0 mg For human use, this tablet is preferably administered 2 to 3 times daily.

We claim:

1. A method for the treatment of convulsions in human beings or animals which comprises administering to a patient suffering from convulsions an anti-convulsive effective amount of a compound of the formula:

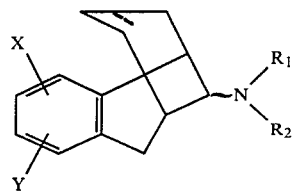

or a pharmaceutically acceptable acid addition salt thereof, wherein $R_1$ and $R_2$ each represent hydrogen or a ($C_1$–$C_4$) alkyl group, the broken line indicates an optional extra bond, and X and Y each represent hydrogen ($C_1$–$C_4$) alkyl or halogen, or a pharmaceutically acceptable acid addition salt thereof.

2. A method according to claim 1, wherein the active ingredient is a compound of the formula:

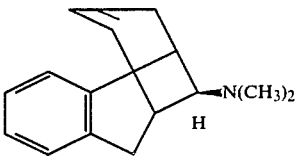

or a pharmaceutically acceptable acid addition salt thereof.

* * * * *